(12) United States Patent
Son et al.

(10) Patent No.: US 8,551,470 B2
(45) Date of Patent: Oct. 8, 2013

(54) USE OF SUBSTANCE P FOR MOBILIZATION OF MESENCHYMAL STEM CELLS OR PROLIFERATION OF MESENCHYMAL STEM CELLS AND FOR WOUND HEALING OR FACILITATING WOUND HEALING

(75) Inventors: Young Sook Son, Seoul (KR); Hyun Sook Hong, Seoul (KR); Jae Chan Kim, Seoul (KR)

(73) Assignees: Korea Institute of Radiological & Medical Sciences, Seoul (KR); Chung-Ang University Industry-Academy Cooperation Foundation, Seoul (KR)

( * ) Notice: Subject to any disclaimer, the term of this patent is extended or adjusted under 35 U.S.C. 154(b) by 630 days.

(21) Appl. No.: 11/259,550

(22) Filed: Oct. 25, 2005

(65) Prior Publication Data
US 2006/0127373 A1     Jun. 15, 2006

(30) Foreign Application Priority Data
Oct. 27, 2004    (KR) .................... 10-2004-0086359

(51) Int. Cl.
*A01N 63/00*     (2006.01)
*A01N 65/00*     (2009.01)
(52) U.S. Cl.
USPC ........................... 424/93.1; 435/325
(58) Field of Classification Search
USPC ........................... 424/93.1; 435/325
See application file for complete search history.

(56) References Cited

U.S. PATENT DOCUMENTS

| | | | |
|---|---|---|---|
| 5,616,562 A | 4/1997 | Murphy et al. | |
| 5,998,376 A | 12/1999 | Witten et al. | |
| 2003/0181386 A1* | 9/2003 | Nishida et al. | 514/15 |
| 2003/0225010 A1 | 12/2003 | Rameshwar | |
| 2004/0214762 A1* | 10/2004 | Demuth et al. | 514/12 |

FOREIGN PATENT DOCUMENTS

| | | | | |
|---|---|---|---|---|
| WO | WO-99/46366 | 9/1999 | | |
| WO | WO-02/43748 A1 | 6/2002 | | |
| WO | WO-02/102835 A2 | 12/2002 | | |
| WO | PCT/EP02/08930 | * | 2/2003 | ............ A61K 31/40 |
| WO | WO-2004/022078 A1 | 3/2004 | | |

OTHER PUBLICATIONS

Trantor et al., The effects of neuropeptides (calcitonin gene-related peptide and substance P) on cultured human pulp cells. J Dent Res. 74(4): 1066-71, 1995.*
Nilsson et al., Stimulation of connective tissue cell growth by substance P and substance K. Nature, 315(6014): 61-3, 1985.*
Bongenhielm et al., Effects of neuropeptides on growth of cultivated rat molar pulp fibroblasts. Regul Pept., 60(2-3): 91-8, 1995.*

(Continued)

*Primary Examiner* — Michael C. Wilson
(74) *Attorney, Agent, or Firm* — Edwards Wildman Palmer LLP; Peter F. Corless; Christine C. O'Day

(57) ABSTRACT

The present invention relates to a use of Substance-P for the manufacture of a medicament for mobilization or proliferation of Mesenchymal stem cells (MSCs) from the bone marrow, or facilitating said mobilization or proliferation, and use of Substance-P for the manufacture of a medicament for wound-healing or facilitating wound-healing.

2 Claims, 8 Drawing Sheets c-kit + cells / peripheral blood
Alkali burn      No burn c-kit + cells / wound bed

(56) References Cited

OTHER PUBLICATIONS

Jiang et al., Regulative effects and significance of substance P on the expression of basic fibroblast growth factor of granulation tissue fibroblasts in vitro, Zhonghua Shao Shang Za Zhi. 19(3): 159-62, Jun. 2003 (one page Abstract in English).*
Kageyama et al., Role of endogenous nitric oxide in airway microvascular leakage induced by inflammatory mediators. Eur Respir J. 10(1):13-19, 1997.*
Lapidot et al., Current understanding of stem cell mobilization: the roles of chemokines, proteolytic enzymes, adhesion molecules, cytokines, and stromal cells, Exp Hematol. Sep. 2002;30(9):973-81, 2002.*
Pereira (PNAS, Feb. 1998, vol. 95, p. 1142-1147).*
Koc (J. Clin. Oncol., 2000, vol. 18, p. 307-316).*
Mackenzie (Blood Cells, Molecules, and Diseases, May/Jun. 2001, vol. 27, No. 3, p. 601-604).*
Devine (Exp. Hematol., 2001, vol. 29, p. 244-255).*
Ballas (J. Cell. Biochem. Suppl. 2002, vol. 38, p. 20-28).*
Horowitz (PNAS, 2002, vol. 99, p. 8932-8937).*
Wu (Transplantation, Mar. 15, 2003, vol. 75, p. 679-685).*
Mahmood (Neurosurg. Sep. 2003, vol. 53, No. 3, p. 697-703).*
Toma (Circulation, 2002, vol. 105, p. 93-98).*
Kopen (PNAS, 1999, vol. 96, p. 10711-10716).*
Kadiyala (Tissue Engineering, 1997, vol. 3, No. 2, p. 173-185).*
DeKok (Clin. Oral Implants Res., 2003, vol. 14, p. 481).*
Noel (Current Opinion Investig. Drugs, Jul. 2002, vol. 3, No. 7, p. 1000-1004).*
Caplan (Tissue Engineering, Jul./Aug. 2005, vol. 11, No. 7/8, p. 1198-1211).*
Granero-Molto (Expert Opin. Biol. Ther. 2008, vol. 8, No. 3, p. 255-268).*
Schwartz (Gene Therapy, 1999, vol. 10, p. 2539-2549).*
Chopp (Neuroreport, 2000, vol. 11, p. 3001-3005).*
Tomita (Circulation, 1999, vol. 100, p. 247-256).*
Shake (Ann. Thorac. Surg., 2002, vol. 73, p. 1919-1926).*
Chen (Circ. Res., 2003, vol. 92, p. 692-699).*
Hyun Sook Hong et al., 2004 Seoul Symposium on Stem Cell Research, XP-00237418, "Novel Role of Substance-p as a Wound Messenger to Mobilize Mesenchymal Stem Cells from Bone Marrow and Recruit to the Wound Site" (2004).
Y. Son et al., IVOS, vol. 45, Suppl. 1, p. U555, XP-009064135, Annual Meeting of the Association-for-Research-in-Vision-and-Ophthalmology, Ft. Lauderdale, FL, "Identification of substance-p as an early inductive cytokine of corneal wound and its possible role in the mobilization of mesenchymal stem cell and corneal wound healing" (2004).

* cited by examiner

Fig. 5b
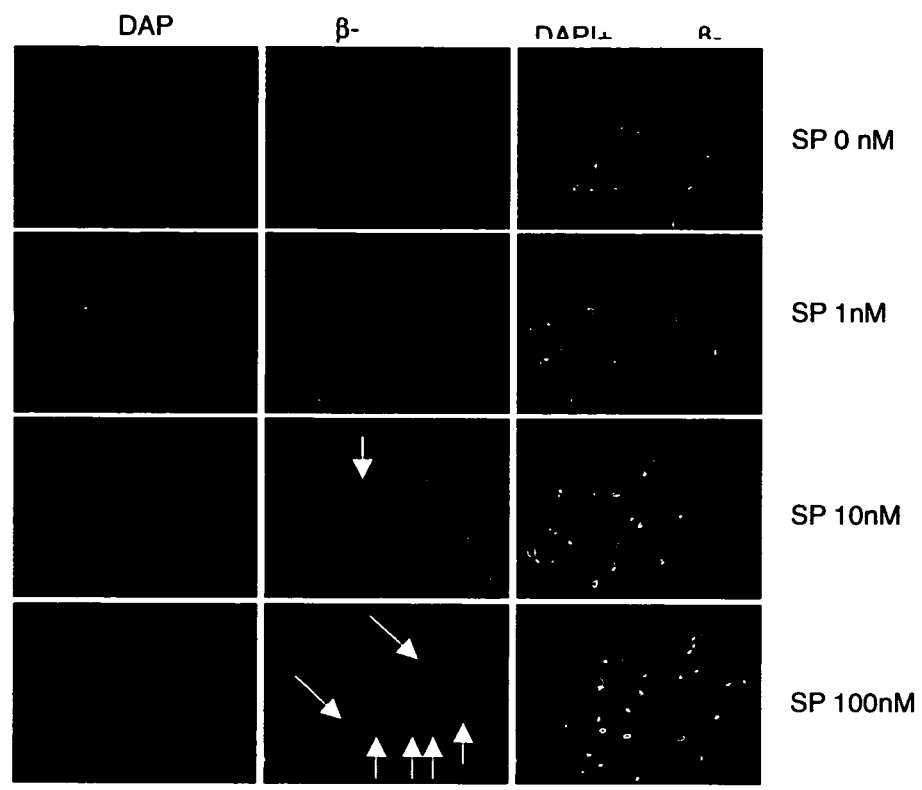
Fig. 5c
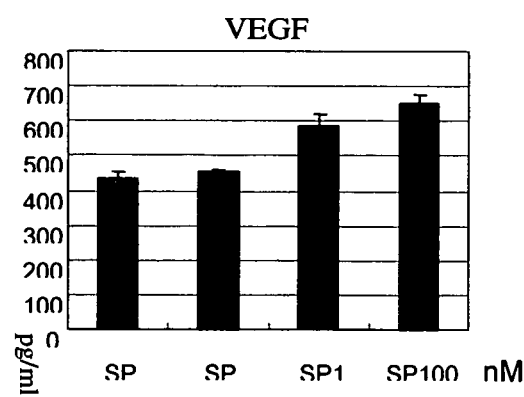
Fig. 5d

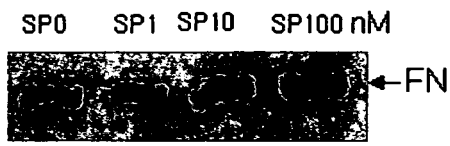
Fig. 6a
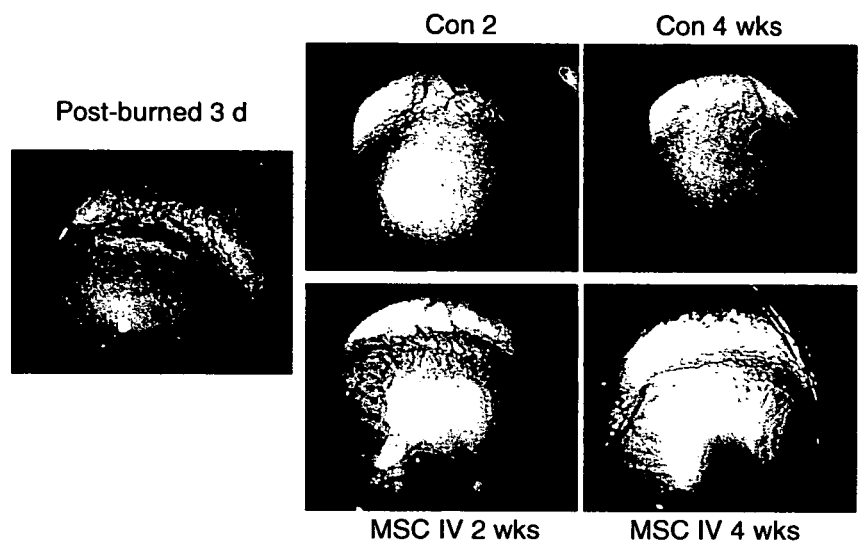
Fig. 6b
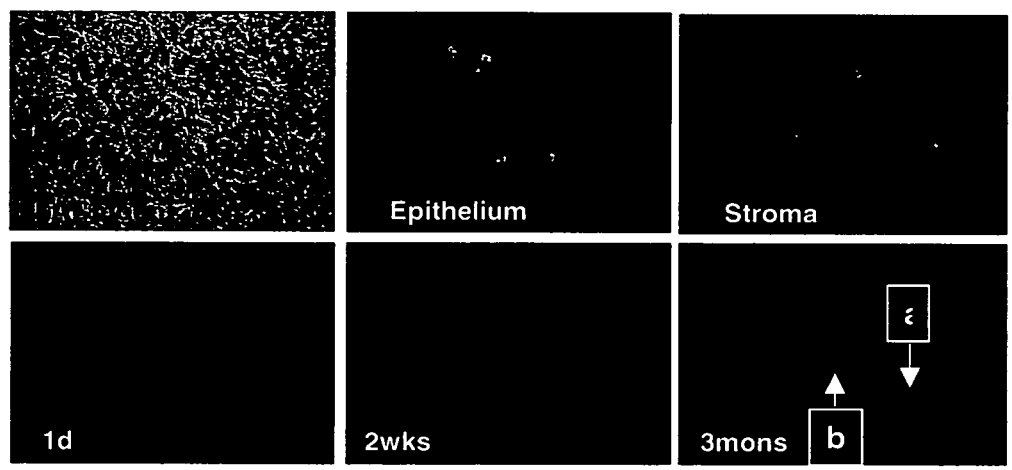

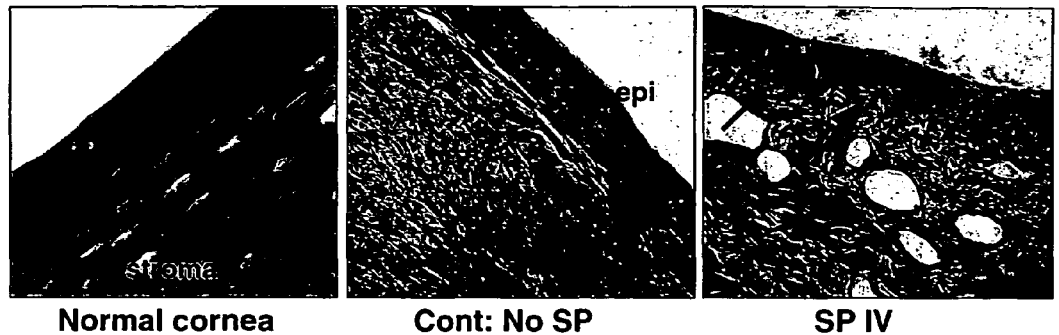
Fig. 7c
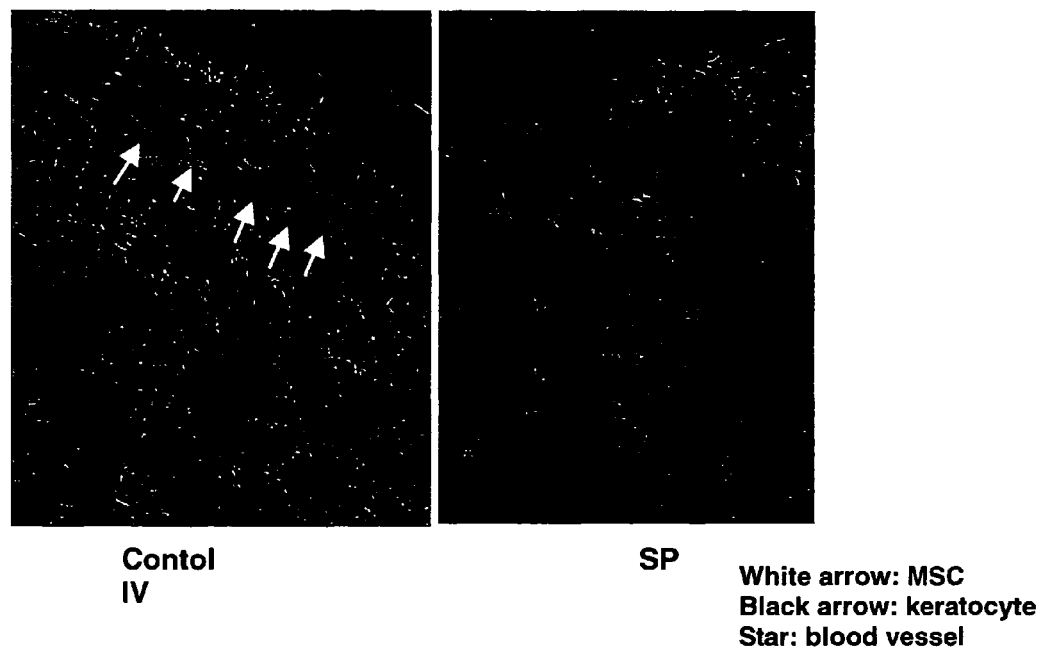
White arrow: MSC
Black arrow: keratocyte
Star: blood vessel

USE OF SUBSTANCE P FOR MOBILIZATION OF MESENCHYMAL STEM CELLS OR PROLIFERATION OF MESENCHYMAL STEM CELLS AND FOR WOUND HEALING OR FACILITATING WOUND HEALING

TECHNICAL FIELD

The present invention relates to a use of Substance-P for the manufacture of a medicament for mobilization or proliferation of Mesenchymal stem cells (MSCs) from a bone marrow, or facilitating said mobilization or proliferation, and use of Substance-P for the manufacture of a medicament for wound-healing or facilitating wound-healing.

BACKGROUND OF THE INVENTION

Substance-P is neuropeptide consisted of 11 amino acids the tachykinin family that is expressed in sensory neurons, macrophages, eosinophils, endothelial cells, and corneal cells such as epithelial cells and keratocytes as well as granulation tissue. Several reports have suggested implication of Substance-P in neuro-immune communication on hematopoietic modulation. The bone marrow stroma was innervated by Substance-P nerve fibers and Substance-P stimulates marrow stromal cells through their surface receptor NK-1 to produce the stem cell factor and interleukin-1, which may be favorable for hematopoietic stimulation as feeders. However, the role of Substance-P in the systemic MSC mobilization and MSC repopulation in the bone marrow has not been reported yet.

A wound itself creates a unique and specific microenvironment that is composed of growth factors, cytokines, neurohormones, and extracellular matrix, all of which are secreted from the neighboring cells, blood born cells, and sensory neurons. Some factors in the wound microenvironment may last sufficiently long to be diffused into the peripheral blood, and in turn affect the stem cells in the bone marrow, to induce mobilization of the bone marrow cells into peripheral blood, supply of the bone marrow cells into the wound site, and participation of the bone marrow cells in the wound healing.

Recent cell transplantation experiments with bone marrow stem cells and cultured MSCs show that they are involved in the tissue repair of lung, gastrointestinal tract, and infarcted myocardium. However, in a normal physiological state without any wound, MSCs are detected in tissues such as fat tissue and pterygium except the bone marrow, but barely in the peripheral blood. Therefore, it is believed that there may be a certain system to mobilize MSCs from the bone marrow into other peripheral tissue during tissue repair and pathological progression.

The cornea is consisted of transparent, avascular and heavily innervated tissue, whose integrity may be broken in case of corneal damage and disease thereof. A corneal wound stimulates lateral movement of the corneal epithelial cells most likely provided by the limbal stem cells, infiltration of the inflammatory cells, and neovascularization in the wound stroma, all of which may be stimulated by the unique corneal wound microenvironment. Previous reports suggest that corneal denervation is a cause of substantial delay in the wound healing process, and the lower level of Substance-P in diabetic patients than non-diabetic patients is also a cause of delayed re-epithelialization and delayed healing. Since the cornea surface is extensively innervated by trigeminal ganglion neurons, and endogenous Substance P is expressed in the corneal epithelial cells and keratocytes, it is expected for Substance P to involve in the wound microenvironment and participate in cornea repair.

SUMMARY OF THE INVENTION

The present inventors discovered that Substance-P is a first neuropeptide which is elevated in eye and peripheral blood in a mouse with corneal alkali burn. Also, they discovered that even though Substance P was injected intravenously into the non-corneal wound mice, many CD29+ MSCs were mobilized into peripheral blood. Further, it was revealed in 3-D collagen gel in vitro that Substance-P stimulates migration of human MSC with induction of matrix degrading enzymes and inhibition of their inhibitor. In addition, they discovered that Substance P stimulates cell proliferation of MSCs, nuclear translocation of $\beta$-catenin, and expression of its target genes, VEGF and fibronectin, and so Substance P may play a role in the bone marrow repopulation of MSCs after their mobilization. Furthermore, the present inventors established that Di 1 labeled MSCs, which were transfused into the ear vein of the alkali burned rabbits, are successfully mobilized at the wound bed and facilitates cornea wound healing with improved corneal transparency and visual recovery. Further, they showed that intravenously-injected Substance-P can facilitate wound healing of alkali burn rabbit eye.

Therefore, the first object of the present invention is to provide a use of Substance-P for the manufacture of a medicament for mobilization or proliferation of Mesenchymal stem cells (MSCs) from the bone marrow, or facilitating said mobilization or proliferation.

The second object of the present invention is to provide a use of Substance-P for the manufacture of a medicament for wound-healing or facilitating wound-healing.

The third purpose of the present invention is to provide an agent for mobilization or proliferation of MSCs from the bone marrow, or facilitating said mobilization or proliferation, containing Substance-P as an effective ingredient.

The fourth purpose of the present invention is to provide a wound healing or facilitating wound healing agent, containing Substance-P as an effective ingredient.

The fifth purpose of the present invention is to provide a wound healing or facilitating wound healing agent, containing MSCs as an effective ingredient, wherein the MSCs are mobilized or proliferated from the bone marrow by treatment of Substance-P.

The sixth purpose of the present invention is to provide a method for separating MSCs, comprising a step of mobilizing MSCs from the bone marrow by Substance-P treatment.

The seventh purpose of the present invention is to provide a method of proliferating MSCs, comprising a step of proliferating MSCs in the presence of Substance-P.

The eighth purpose of the present invention is to provide a method of healing wound or facilitating wound-healing, comprising administering a therapeutically effective amount of Substance-P.

The ninth purpose of the present invention is to provide a method of healing wound or facilitating wound-healing, comprising administering a therapeutically effective amount of MSCs, wherein the MSCs are mobilized or proliferated from the bone marrow by treatment of Substance-P.

The application file contains at least one drawing executed in color. Copies of this patent application publication with color drawings will be provided by the U.S. Patent and Trademark Office upon request and payment of the necessary fee.

BRIEF DESCRIPTION OF THE DRAWINGS

FIG. 5b shows result of immunofluorescence staining with β-catenin antibody in human MSCs cultured in the presence of Substance-P (0-100 nM).

FIG. 5c is a graph of ELISA analysis result of VEGF collected from culture supernatants of Substance-P treated human MSCs.

FIG. 5d shows results of Western blot analysis with monoclonal antibody against human fibronectin from the culture supernatant of Substance-P treated human MSCs.

FIG. 6a shows a photo of slit-lamp examination result of the rabbit eye at 14, 30 days after corneal alkali burn with or without transfusion of Di 1 labeled rabbit MSCs.

FIG. 6b shows a photo of existence of Di 1 labeled MSCs in cornea observed by flat mount examination with fluorescent stereoscopic microscope.

FIG. 7c shows a photo of immunohistochemical staining with CD-29 antibody in the tissue section after corneal alkali burn with or without intravenous injection of Substance-P.

DETAILED DESCRIPTION OF THE INVENTION

Figure 1:
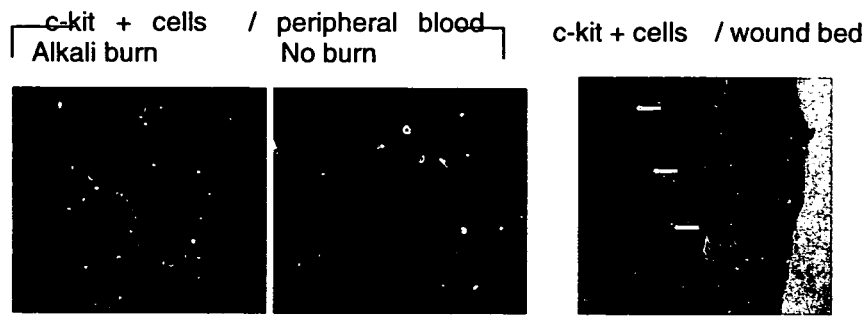
FIG. 1 shows elevation of c-kit+ stem cells in the peripheral blood and wound bed of a rabbit after corneal alkali burn (c-kit positive cells at the wound bed are shown by arrows).

First, the present invention relates to a use of Substance-P for the manufacture of a medicament for mobilization or proliferation of Mesenchymal stem cells (MSCs) from the bone marrow, or facilitating said mobilization or proliferation. In an embodiment, said medicament may comprise MSCs. In another embodiment, said medicament may be a cellular therapeutic agent.

Second, the present invention relates to a use of Substance-P for the manufacture of a medicament for wound-healing or facilitating wound-healing, for example, cornea and skin wound. In an embodiment, said medicament may comprise MSCs. In another embodiment, said medicament may be a cellular therapeutic agent.

Third, the present invention relates to an agent for mobilization or proliferation of MSCs from the bone marrow, or facilitating said mobilization or proliferation, containing Substance-P as an effective ingredient.

Forth, the present invention relates to a wound healing or facilitating wound healing agent, containing Substance-P as an effective ingredient, for example, for cornea and skin wound.

Fifth, the present invention relates to a wound healing or facilitating wound healing agent, containing MSCs as an effective ingredient, wherein the MSCs are mobilized or proliferated from the bone marrow by treatment of Substance-P.

Sixth, the present invention relates to a method for separating MSCs, comprising a step of mobilizing MSCs from the bone marrow by Substance-P treatment.

Seventh, the present invention relates to a method of proliferating MSCs, comprising a step of proliferating MSCs in the presence of Substance-P.

Eighth, the present invention relates to a method of healing wound or facilitating wound-healing, comprising administering a therapeutically effective amount of Substance-P.

Ninth, the present invention relates to a method of healing wound or facilitating wound-healing, comprising administering a therapeutically effective amount of MSCs, wherein the MSCs are mobilized or proliferated from the bone marrow by treatment of Substance-P.

Below, the present invention is described in detail.

The present inventors used alkali burn cornea animal model which has advantages in examining systemic participation of stem cells during the wound healing process over other wound model since cornea has transparency and avascularization.

After observing advent of c-kit+ cells in cornea and peripheral blood of rabbit with corneal alkali burn, the expression profiles of the cytokines and other factors in the wound microenvironment and the peripheral blood in the mice with a corneal alkali burn were examined by using RT-PCR analysis and ELISA. As a result, it was revealed that Substance-P is the first neuropeptide whose expression is elevated in the cornea wound as well as in the peripheral blood of the mice with corneal alkali burn. At this time, Substance-P was first increased in cornea and later in peripheral blood. It shows that Substance-P is provided by the corneal resident cells such as the sensory neurons, epithelial cells, keratocytes, and endothelial cells, not by infiltration of neutrophils or macrophages. The increase of Substance-P concentration in blood may be from systemic diffusion of Substance-P. Also, lack of Substance-P immunoreactivity in the neutrophils, earlier induction and termination of Substance P than duration of the inflammatory phase (up to 5 days after wound), and the weak Substance-P staining in the epithelial cells and fibroblastic cells at the later stage of wound healing (7-10 days after wound) supports an assumption that Substance-P is provided by nociceptive stimulation of the sensory neurons.

Subsequently, in order to determine the systemic effect of Substance P separately from the other factors that are found in the wound microenvironment, Substance P was injected intravenously into the mice without wound, and the mobilization of CD29+ MSCs into peripheral blood was examined. As a result, it was observed that approximately 15 times more CD29+ MSCs are mobilized into the peripheral blood in mice into which Substance-P was injected intravenously, than in the non-injected mice. Here, it is believed that MSCs in non-wound mice were mobilized to peripheral blood because there was no wound site for MSCs to mobilize in the absence of wound bed.

Also, to determine the action mechanism of Substance P in MSC mobilization from the endosteal surface of the bone marrow, an in vitro cell migration assay was used, and the effect of Substance-P on the MSC migration, dynamics of matrix degrading enzyme, cell proliferation and β-catenin localization were examined. As a result, it was revealed that in 3-D collagen gel in vitro, Substance-P induces matrix degrading enzymes and inhibits their inhibitors, thereby stimulating migration of human MSCs. This result further supports the role of Substance-P in MSCs migration. Also, the inventors discovered that Substance-P stimulates cell proliferation and nuclear translocation of β-catenin, thereby promoting the bone marrow repopulation of MSCs after the mobilization of MSCs.

Furthermore, the present inventors examined whether or not intravenously injected MSCs arrive at damaged tissue and are involved in repair of the cornea, based on the corneal transparency and vision recovery scores. As a result, they confirmed that Di 1-labeled MSCs, which were transfused into the ear vein of alkali burned rabbits, are successfully supplied to the wound bed and improve corneal transparency and visual recovery, thereby facilitating cornea wound healing.

Finally, the present inventors examined whether or not intravenous injection of Substance-P can facilitate corneal wound healing, based on macroscopic examination, H&E staining, and immunohistochemical staining. As a result, compared with the control group (Substance-P non-injected group), healing of the corneal wound in Substance-P-injected group was progressed rapidly.

In conclusion, it was discovered that Substance-P is first elevated in the cornea wound and the peripheral blood, and facilitates mobilization of MSCs to peripheral blood, and promotes healing of the corneal wound and proliferation of MSCs in the bone marrow.

Thus, it was concluded that Substance-P plays a role as wound signaling initiator to involve in mobilization and supply of MSCs from the bone marrow to the wound site. Also, it was identified that MSCs mobilize to wound site and are involved in wound healing.

Considering the above results, MSCs can be used as wound healing or facilitating wound healing medicament, or cellular treatment medicament. Also, Substance-P can be used as wound healing or facilitating wound healing agent, or cellular treatment medicament, or mobilization, or proliferation medicament, or facilitating mobilization or proliferation medicament, of MSCs.

In the present invention, the effective dosage of Substance-P is 0.1 μg/kg to 100 μg/kg, and the effective dosage of MSCs is $3\times10^4$ cells/kg to $3\times10^7$ cells/kg, particularly, $1\times10^5$ cells/kg to $1\times10^7$ cells/kg. However, these dosages can be modified depending on weight, age, sex or extent of wound of patients.

A formulation according to the present invention can be administered into human bodies parentally or locally, for example, by intravenous injection, subcutaneous injection, endodermis injection, and muscular injection. Preferably, they are administered by intravenous injection. For this purpose, the effective ingredients are suspended or dissolved in a pharmacologically acceptable carrier, preferably, water-soluble carrier.

Below, the present invention is more specifically explained by the following Examples, but it is not intended to limit the scope of the present invention in any way.

EXAMPLES

Example 1

Identification of Elevation of C-Kit Positive Stem Cells in Peripheral Blood and their Supply to the Would Bed after Corneal Alkali Burn New Zealand white rabbits weighing 2-3 kg were purchased from Samtako BioKorea. All these animal experiments were approved by Ethical Committee, Korea Institute of Radiological and Medical Sciences, and Chung-Ang University, and conducted in accordance with the ARVO Statement for the Use of Animal in Ophthalmic and Vision Research. For the alkali burn, the rabbit eyes were placed in contact with a 6 mm piece of circular Whatman filter paper soaked in 1N NaOH for 30 seconds. At 1, 3, 5, 7, 10 and 14 day after the alkali burn, rabbit eyes and whole blood were isolated. The smears of blood and cornea section were stained with Anti-C kit antibody, and this result was shown in FIG. 1.

Intact cornea is avascular tissue, and so extensive damage thereto might require vascular supply of inflammatory cells and other stem cells for the corneal repair. As shown in FIG. 1, when the alkali burn was done on the rabbit cornea, the number of c-kit positive cells was increased in the peripheral blood, compared with the normal control, which was also detected in the corneal wound bed at 5th day after the alkali burn. This result confirms that stem cells originating from the bone marrow may actively participate in the repair of the cornea.

Example 2

Identification of Role of Substance-P as Wound Signaling Initiator Induced by Cornea Alkali Burn Balb/c mice weighing 30-40 g were purchased from Jackson Lab (West Grove, Pa.). For the alkali burn, the mouse eyes were placed in contact with a 3 mm piece of circular Whatman filter paper soaked in 1N NaOH for 10 seconds. At 1, 3, 5, 7, 10, and 14 day after the alkali burn, the mouse eyes and whole blood were isolated.

Tissue damage itself may constitute a unique wound microenvironment to induce a systemic response such as inflammation and stem cell mobilization from the bone marrow to repair the damaged tissue. RT-PCR was used to analyze candidate factors retaining these functions in the wound microenvironment of alkali burned cornea. Specifically, RNA was isolated from the alkali burned eye by Trizol (Invitrogen). Total 1 μg of RNA was reverse transcribed (RT) by using reverse transcription-polymerase kit (Takara), followed by PCR by using mouse gene-specific primers as follows:

```
VEGF (expected size: 407),
                                        (SEQ ID NO: 1)
(sense)         5'GTACCTCCACCATGCCAAGT3',
                                        (SEQ ID NO: 2)
(antisense)     5'AATGCTTTCTCCGCTCTGAA3',
```

-continued

```
TNF-alpha (expected size: 438),
                                       (SEQ ID NO: 3)
(sense)             5'GAACTGGCAGAAGAGGCACT3',
                                       (SEQ ID NO: 4)
(antisense)         5'GTGGGTGAGGAGCACGTAGT3', IL-1 (expected size: 432),
                                       (SEQ ID NO: 5)
(sense)             5'GCTGCTTCCAAACCTTTGAC3',
                                       (SEQ ID NO: 6)
(antisense)         5'AGGCCACAGGTATTTTGTCG3', Substance-P (expected size: 309),
                                       (SEQ ID NO: 7)
(sense)             5'TCGATGCCAACGATGATCTA3',
                                       (SEQ ID NO: 8)
(antisense)         5'AGTTCTGCATTGCGCTTCTT3'
```

Figure 2A:
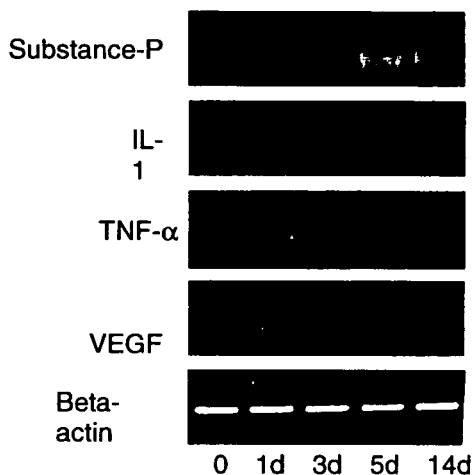
FIG. 2a shows results of RT-PCR analysis of the mouse eyes after corneal alkali burn.

The result of PCT is shown by FIG. 2a. As shown in FIG. 2a, it was found that Substance-P, IL-1, TNF-α and VEGF are induced in the eye after the cornea wound.

Figure 2B:
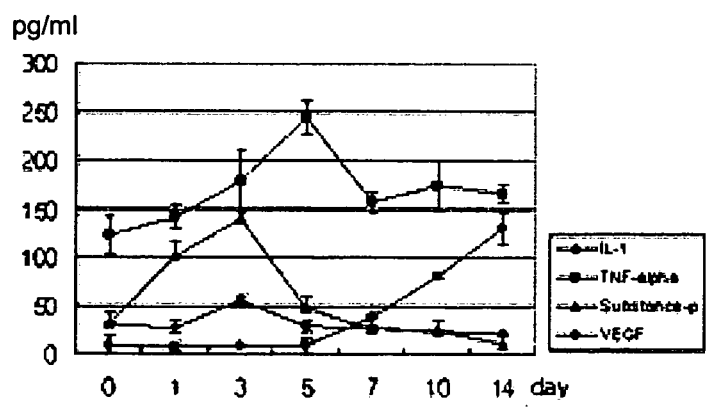
FIG. 2b shows results of ELISA analysis of the peripheral blood of the mice collected at 0, 1, 3, 5, 7, 10, 14 days after corneal alkali burn.

In order to further monitor the systemic profile of these factors and assess their possible roles in stem cell mobilization from the bone marrow, ELISA (R&D system) to the peripheral blood was performed. The result is shown in FIG. 2b. As shown in FIG. 2b, compared with the non-wound state, the level of Substance-P in the serum was elevated by approximately 3.2. times at 1 day, 4.4 times at 3 day, and 1.3 times at 5 day. However, pre-inflammatory cytokines, TNF-a, and IL-1 induction were detected at 5 day and 3 day after the alkali burn, respectively, and VEGF was induced from 7 day much later than them.

For the histological examination, Hematoxylin and Eosin (H&E) staining was performed for corneal wound bed, and immunohistochemical staining was performed with Substance-P antibody (Santa Cruz Biotechnology: Cat #sc-9758, 1:200). The mouse eyes were fixed with 4% of paraformaldehyde for 48 h. The paraffin-embedded specimens were cut longitudinally into 4-µm sections, and transferred to poly-D lysine-coated slides. Then, Hematoxylin and Eosin (H&E) staining was performed for the histological examination. For immunohistochemical staining of Substance-P, the endogenous peroxidase activity was blocked by incubation with 0.5% of $H_2O_2$ for 10 min. The tissues were then permeabilized with 0.3% of Triton x-100 for 5 min, and incubated with the primary antibodies, the remaining procedures were followed by the manufacturer's specifications (ABC kit, Vector), and the cells were counterstained with fast red.

Figure 2C:
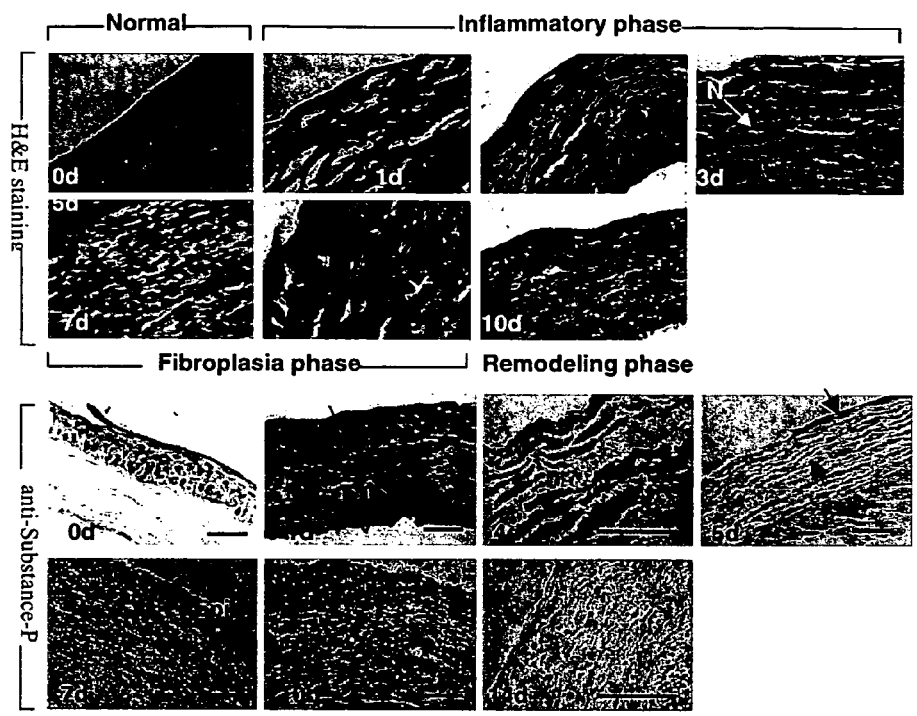
FIG. 2c shows results of Hematoxylin & Eosin staining, and immunohistochemical staining with Substance-P antibodies in the wound bed after the alkali burn in the mouse eye.

The result is shown in FIG. 2c. As a result of H&E staining, the inflammatory neutrophils were sustained for up to 5 days, the migrating epithelial cells were discernible at 5 day, fibroblastic infiltration was obvious at 7 day, and most macrophages had disappeared at 14 day. The immuno-reactive Substance-P was most strongly detected in the wound bed after 1 day and became weaker till 3rd day. At 5th day, Substance-P was barely detected in the fibroblastic cells and migrating epithelial cells, but was not detected in the inflammatory cells, which suggests that the early inflammatory cells may not secrete Substance-P. Therefore, the cornea wound itself appears to create a Substance-P rich microenvironment possibly provided by cornea resident cells, which may in turn induce the Substance-P elevation in the serum.

Figure 2D:
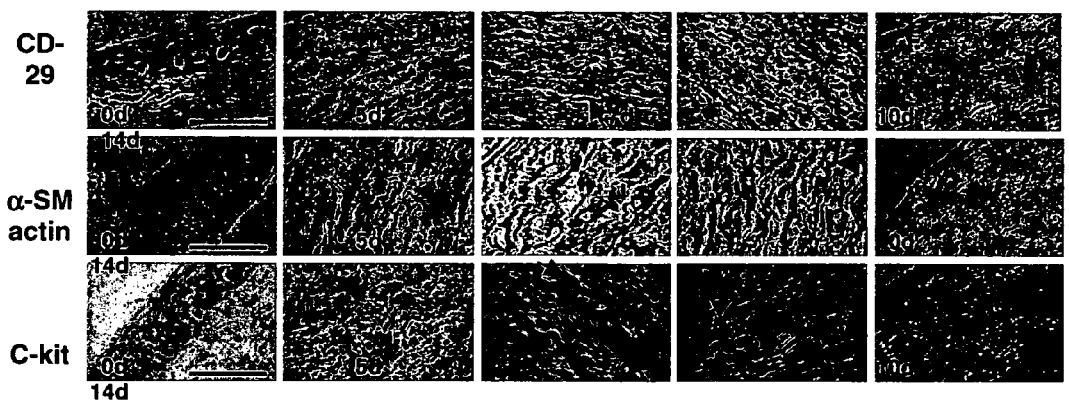
FIG. 2d shows results of immunohistochemical staining with c-kit, CD-29, and α-SM actin antibodies in the wound bed after the alkali burn in the mouse eye.

In order to determine whether the MSCs derived from bone marrow are supplied to a wound site, immunohistochemical staining was performed with the MSC markers, anti-CD-29 (Santa Cruz Biotechnology; Cat #sc-6622, 1:200), anti-c-kit (Santa Cruz Biotechnology; Cat #sc-1493, 1:100), and anti-a-SM actin antibodies (Progen, Cat #61001, 1:200). The result is shown in FIG. 2d. As known from FIG. 2d, the CD-29, c-kit, and α-SM-actin expressing fibroblastic cells were not detected at the early inflammatory phase until 5th day. They were detected at the wound bed from 7th day to 10th day corresponding to the fibroplasias phase, and had mostly disappeared after 14th day corresponding to the remodeling phase. This result is correlated with the absence of fibroblastic cells in the wound bed at the early phase of wound healing and the first emergence of fibroblastic cells in the wound bed at 7th day. Since only a few fibroblastic cells were present in the normal corneal stroma (FIG. 2c) and the resident fibroblastic cells were absent at the inflammatory phase before 7 day, the CD-29, α-SM-actin, and c-kit positive cells in the 7th day wound bed were probably MSCs that were imported from the blood.

Example 3

Identification of Mobilization of MSCs from the Marrow into Peripheral Blood by Intravenous Injection of Substance-P Substance-P was examined to determine whether it is responsible for stem cell mobilization into the blood stream or whether some other unidentified factors in the wound microenvironment are involved in stem cell mobilization.

In order to distinguish effects of the others factors in the wound microenvironment, Substance-P (0.1 nmole/g of body weight) (Calbiochem) was injected intravenously through tail vein in Balb-c mice without causing alkali burns to the eye, and then the whole blood was collected after 1 day. After removing red blood cells by percoll gradient centrifugation, the attached cells were cultured for 48 h in order to remove lymphocytes, and then, in order to distinguish MSCs from the lymphocytes, they were immune-stained with antibodies against CD-29 (β1 integrin) which is not expressed in the macrophages.

Figure 3A:
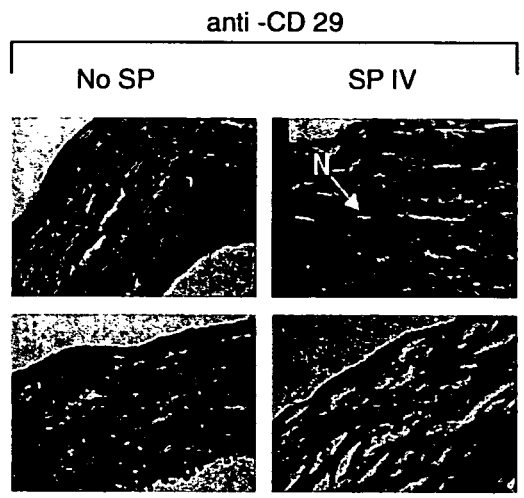
FIG. 3a shows results of immunocytochemical staining with CD-29 antibodies in the attached cells isolated from the mouse blood after intravenous injection of Substance-P.
Figure 3B:
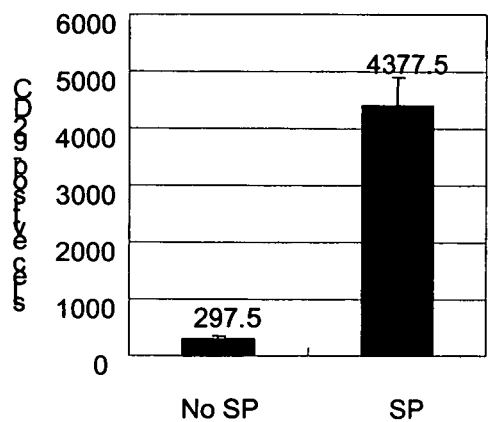
FIG. 3b is a graph showing mean numbers of CD-29+ cells in the blood before or after intravenous injection of Substance-P.

The result is shown in FIGS. 3a and 3b. Within 1 day, the intravenous injection of Substance-P strongly stimulated mobilization of CD-29 positive MSCs into the peripheral blood approximately by 15 times more than in the non-injected mice (FIG. 3b). This shows a new role of Substance-P which may be manifested during early phase of the wound healing process, to mobilize MSC from the bone marrow into the systemic blood, to supply MSCs to the cornea wound site, and to facilitate the cornea repair.

Example 4

Identification of MMP Activity Elevation by Substance-P

Figure 4A:
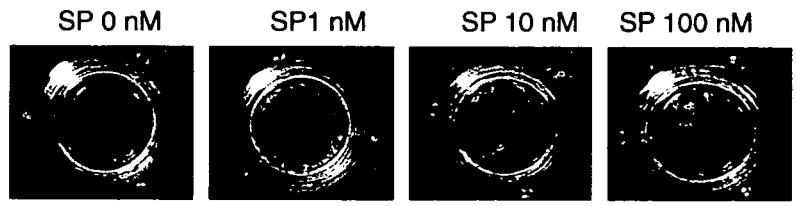
FIG. 4a shows the results of transmigration and collagen degradation of human MSCs on the 3-D collagen gel in response to Substance-P treatment.

In order to determine the mechanism of Substance-P in the mobilization of MSCs, which are strongly attached onto the endosteal surface of bone marrow, Substance-P was first examined to determine whether it stimulates migration of human MSCs cultured on top of the 3-D collagen gel. The type I collagen gel matrix was made within a 12 mm millicell membrane (milipore: 12-µm pore size) according to the manufacturer's specifications (Nitta gelatin, Japan) and coated overnight with type IV collagen (Nitta). The MSCs were plated on top of the collagen gel, and the outer chamber was filled with Substance-P-containing MSCGM (Cambrex Bio Science). Clearance of the collagen gel was monitored by using the phase contrast microscopy (Olympus). At 72 h, the millicell insert and outer dishes were fixed and stained with hematoxylin, and then the culture supernatants were stored for gelatin zymography. This result is shown in FIG. 4a. As shown in FIG. 4a, Substance-P applied into the bottom dishes stimulated degradation of the collagen gel and MSC migration in a dose dependent manner.

Figure 4B:
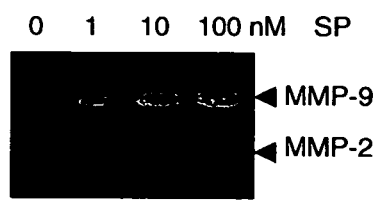
FIG. 4b shows results of gelatin zymography of culture supernatants collected from human MSC culture on the 3-D collagen gel after the treatment of Substance-P (0-100 nM).

The culture supernatants were examined for gelatin zymography. The eletrophoresis was performed for the culture supernatant in which sample buffer without mercaptoethanol was added thereto, in 8% SDS-PAGE. The gel was renatured with 2.5% of Triton x-100 in order to remove the SDS, and then was incubated with a developing buffer (50 mM Tris-HCl, pH 7.2 100 mM NaCl, 20 mM $CaCl_2$) at 37° C. overnight, and the gel was stained with Coomassie blue. This result is shown in FIG. 4b. As shown in FIG. 4b, gelatin zymography of the culture medium revealed strong induction of MMP-9 and MMP-2 activities during MSC migration.

Figure 4C:
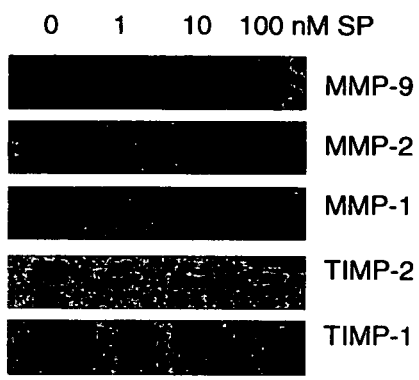
FIG. 4c shows results of immunoprecipitation with antibodies against MMP-1, MMP-2, MMP-9, TIMP-1 and TEMP-2 in the culture supernatant collected from human MSCs after the treatment of Substance-P (0-100 nM).

The effect of Substance-P on the biosynthesis of MMPs (matrix metalloproteinases) and their inhibitors was examined by immunoprecipitation of the culture medium and the cell lysates of MSCs which were labeled with $^{35}$S-methionine. The MSCs were treated with Substance-P and labeled with 50 μCi/ml $^{35}$S-methionine (Amersham) for 16 h. The cell lysate was prepared with a lysis buffer (1% of NP40, 10 mM Tris-HCl, pH 7.4, 150 mM NaCl, 1 mM EDTA, 2 mM PMSF). For immunoprecipitation of the secreted MMP-1, MMP-2, MMP-9, TIMP-1 and TIMP-2, the culture supernatants were incubated with their specific antibodies [anti-MMP-1 (chemicon; Cat #MAB3307, 1:100), anti-MMP-2 (Chemicon; Cat #MAB13405, 1:200), anti-MMP-9 (Calbiochem; Cat #444236, 1:100), anti-TIMP-1 (Calbiochem; Cat #IM32L, 1:250) and anti-TIMP-2 (Calbiochem; Cat #IM11L, 1:250)] for 2 h under constant rotation, and the antibodies were collected by protein-G sepharose-4B (Biorad). The pellet was washed three times with an immunoprecipitation buffer (150 mM NaOH, 50 mM Tris-HCl pH 7.4, 0.2% SDS and 0.5% Nadeoxycholate), once with a high salt buffer (10 mM Tris-HCl, pH 7.4, 0.5 M NaCl), and once with a low salt buffer (10 mM Tris-HCl, pH 7.4). After SDS-PAGE, the gel was soaked in 2 M sodium salicylate, dried, and exposed to the X-ray film for 2 weeks. For immunoprecipitation of MMP-9, the cell lysate was incubated with MMP-9 antibodies, and the remaining procedures were the same as described above. This result is shown in FIG. 4c.

The biosynthesis of MMP-1, MMP-2, MMP-9, and MT1-MMP was stimulated in a dose dependent manner. In contrast, the biosynthesis of their inhibitors, TIMP-1 and TIMP-2, was inhibited by Substance-P.

As a result, Substance-P stimulated MSC migration in 3-D collagen gel, induction of MMPs, and inhibition of their inhibitors, TIMPs.

Example 5

Identification for Facilitation of MSC Repopulation by Substance-P

If Substance-P only has capacity of MSC mobilization from the bone marrow, the bone marrow stroma may become empty in the MSC pool after the mobilization. The effect of Substance-P was again examined about its cell proliferation and self-renewal capacity.

Figure 5A:
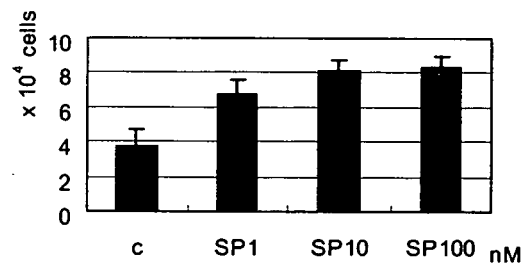
FIG. 5a is a graph to show numbers of viable human MSCs after the Substance-P treatment (n=4, mean number±S.D).

At 3 day after the treatment of Substance-P, the triphan blue excluded viable cells were counted. The result is shown in FIG. 5a.

Substance-P increased the number of viable cells, 1.7 times at 1 nM, 2.1 times at 10 nM, and 2.2 times at 100 nM, compared with the control group.

In order to determine whether Substance-P affects the self-renewal capacity of human MSCs, β-catenin, which is the downstream effecter of the wnt signaling pathway, was examined. MSCs (Cambrex Bio Science) were plated in the density of $1\times10^4$/well, and incubated with MSCGM (Cambrex Bio Science). After adhesion of the cells, they were treated with Substance-P in each concentration, and incubated for 16 h and 48 h. The MSCs were fixed with 4% of paraformaldehyde and permeabilized with 0.3% of Triton X-100. After blocking nonspecific antigen with 20% normal goat serum which was diluted in phosphate buffer for 1 h, the coverslips were incubated with antibodies against β-catenin (BD Biosciencs; Cat #6010153, 1:100) for 90 min, and then with the FITC-conjugated secondary antibodies for 60 min(Vector). The cells were counterstained with DAPI, and examined by using confocal microscopy (Leica). This result is shown in FIG. 5b.

At 16 h after the Substance-P treatment, β-catenin was mainly observed in the cytoplasm of human MSCs, but only a small number of MSCs at 100 nM showed nuclear localization of β-catenin. However, at 48 h after Substance-P treatment, the nuclear translocation of β-catenin was more prominent, and particularly at 100 nM of Substance-P treatment, all the MSCs showed nuclear translocation of β-catenin.

ELISA and Western blot analysis of fibronectin and VEGF, which are down stream genes of Tcf/β-catenin, were carried out. These results are shown in FIGS. 5c and 5d.

As shown in FIGS. 5c and 5d, Substance-P induced VEGF and fibronectin. This proves that Substance-P plays a role in repopulation of the remaining MSCs by the stimulation of cell proliferation or self-renewal via well-known canonical wnt signaling pathway.

In conclusion, Substance-P stimulated cell proliferation, translocation of β-catenin, and induction of β-catenin downstream gene, VEGF and fibronectin, all of which suggest that Substance-P plays a role in repopulation of the bone marrow.

Example 6

Identification for Supply of I.V.-Injected MSCs to the Cornea Wound Bed and Improvement in the Vision Recovery As shown in FIG. 3, intravenous injection of Substance-P was sufficient to stimulate mobilization of mouse CD-29+ MSCs into the peripheral blood. In order to examine whether or not the mobilized MSCs can actually participate in cornea wound healing, Di 1-labeled MSCs were transfused to the ear vein of the non-irradiated rabbit at 24 h after the cornea alkali burn to minimize the MSC homing to the bone marrow and to maximize the supply into wound site.

The MSCs were isolated from the tibia of a 1 month old allogenic rabbit by bone marrow irrigation and aspiration, and cultured with MSCGM up to passage 3. The attached cells were identified as MSCs by the expression of c-kit, STRO-1, and a-smooth muscle (SM) actin, and were used for the cell transfusion experiment. In order to trace the transfused MSCs, the trypsinized cells were incubated with a Di 1 solution [Celltracker™ CM-Di I (Cat#C-7000); Molecular Probes] for 5 min at 37° C. and 15 min at 4° C. After labeling and subsequent washing with PBS three times, the MSCs ($1\times10^6$ cells/ml) were resuspended in fresh serum free medium and injected into the ear vein of 10 rabbits at 1 day after the corneal alkali burn.

In 2 weeks and 4 weeks after the alkali burn wound, the eyes of the non-injected group and MSC-injected group labeled with Di I were examined by slit lamp. This result is shown in FIG. 6a. The corneal visual recovery was better in the MSC injected group than in the non-injected group.

The epithelial healing time was determined by closure of the epithelial defect with photo-slit microscopic examination and photo-documentation. The corneal opacity was graded according to the following criteria: grade 0—no opacity, grade 1—the iris structure is visible with mild opacity, grade 2—the fine iris structure is not visible, grade 3—only the presence of the iris is noted as brown color, and grade 4—totally opaque. This result is shown in Table 1.

TABLE 1

|  | the epithelial healing time (day) | corneal opacity | corneal neovascularization |
|---|---|---|---|
| control group (n = 10) | 10.25 ± 2.36 | 3.43 ± 0.79 | 3.57 ± 0.79 |
| MSC IV (n = 10) | 5.50 ± 0.58* | 1.50 ± 0.65* | 1.71 ± 0.75* |

*p < 0.05

As shown in Table 1, the MSCs-injected rabbits showed 2-fold shortening of the epithelial healing time, better corneal transparency, and less corneal neovascularization than the non-injected group.

FLAT mount was performed in order to confirm whether or not the transfused Di 1 labeled-MSCs are localized to the wound bed. In order to identify the Di 1 labeled-MSCs in the cornea, FLAT mounts at 1 day and in 2 weeks and 3 months were examined by fluorescence stereomicroscopy (Leica). This result is shown in FIG. 6b. As shown in FIG. 6b, the Di 1-labeled MSCs were detected at the epithelium level as well as at the stroma level. Di 1-labeled MSCs were detected at the wound bed as early as 1 day after the intravenous transfusion, and their presence was detected even after 3 months from the transfusion though the intensity of Di 1 was lower.

Example 7

Figures 7A, 7B:
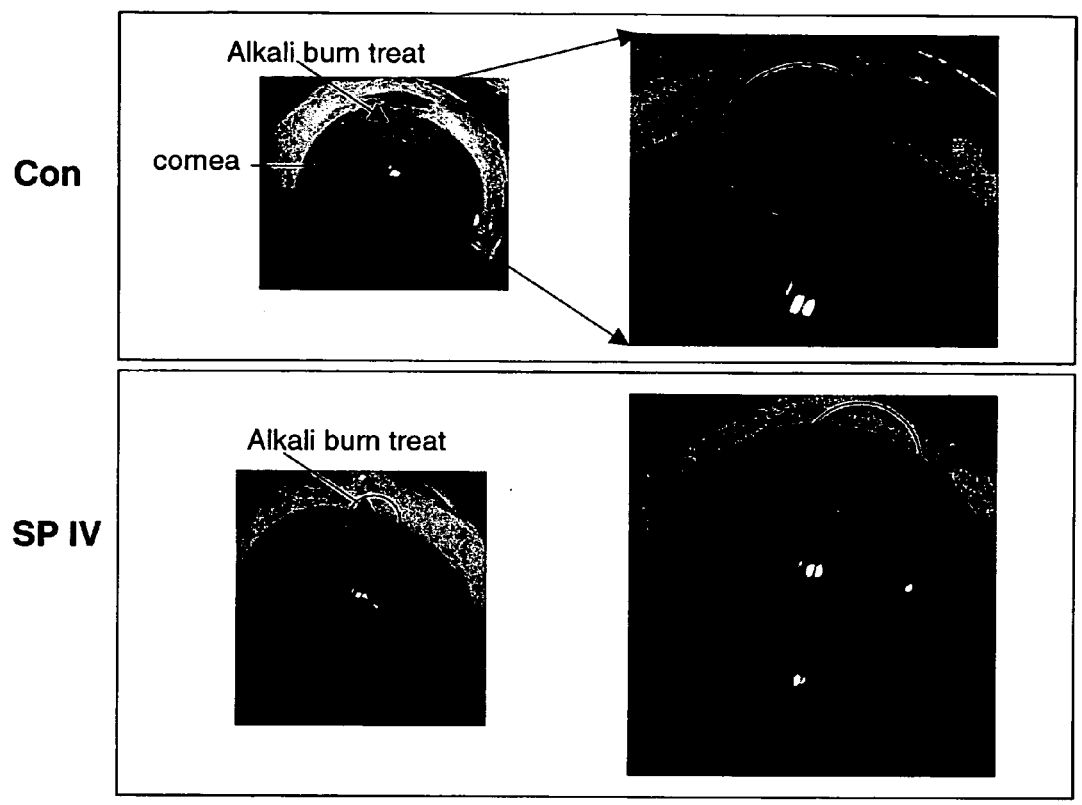
FIG. 7a shows a photo of the corneal wound recovery after corneal alkali burn in rabbit with or without intravenous injection of Substance-P.
FIG. 7b shows a photo of H&E staining result of the tissue section after corneal alkali burn with or without intravenous injection of Substance-P

Identification for Facilitation of Cornea Wound Healing by Intravenous Injection of Substance-P As shown in FIG. 3, intravenous injection of Substance-P was sufficient to faciliate the mobilization of mouse CD-29+ MSCs into the peripheral blood, and as shown in FIG. 6, intravenous injection of Substance-P improved corneal vision recovery. Thus, it was examined whether or not Substance-P only can stimulate corneal wound healing. To estimate the effect of Substance-P intravenous injection on acceleration of the wound healing, Substance-P at dosage 6.5 ug/kg was intravenously injected firstly immediately after the injury, and then secondly on 2nd day after the wound. At day 7 after the intravenous injection, cornea recovery was estimated by naked eyes with taking digital picture. This result is shown in FIG. 7a. As shown in FIG. 7a, the corneal regeneration was much faster in the Substance-P-injected rabbit than the non-injected control group. The intravenous injection of Substance-P strongly expedited the cornea healing as shown by clearance of corneal opaqueness and disappearance of hemorrhagic area, compared with the non-injected control rabbit.

To observe the wound healing degree in the histological level, rabbit eyes were isolated and fixed, and then, H&E staining and immunostaining for CD29 were carried out. The result of H&E staining is shown in FIG. 7b. As shown in FIG. 7b, the Substance-P-injected group showed full thickness coverage of epithelium, well organized vasculature, and ordered array of dense collagen bundles, which are similar to those of the non-injured collateral side except the still presence of macrophages and polymorphonuclear giant cells beneath the epithelium. In contrast, the non-injected rabbit on the same day showed only thin coverage of epithelium, active infiltration of large fibroblast like cells, and loose unorganized collagen fibrils in the stroma, which are similar to those observed on 5 day in the Substance-P injected group.

The result of CD29 staining is shown in FIG. 7c. As shown in FIG. 7c, the non-injected group showed undifferentiated mesenchymal stem cell (CD29-expressing cells) but, the Substance-P-injected group showed CD 29+cells of small and spindle shape inside of collagen fibers, which is similar to normal cornea stroma. Thus, comparing the histological observation between the Substance P-injected and the non injected cornea during the entire period, it is confirmed that SP IV injection speeded up the healing rate faster than the control group. These results mean that injection of Substance-P is effective to corneal wound healing.

According to the present invention, Substance-P is initially elevated in the alkali burned cornea, and mobilized into the bone marrow through blood, and then stimulates mesenchymal stem cell in the bone marrow, and induces repopulation of MSCs in the bone marrow.

Thus, Substance-P can be utilized as wound healing or facilitating wound-healing agent, mobilization or proliferation or facilitating mobilization or proliferation agent, of MSCs.

Also, MSCs are confirmed to directly involve in wound healing. Thus, MSCs can be utilized as wound healing or facilitating wound healing agent, or cellular therapeutic agent.

What is claimed is:

1. A method of healing a corneal wound in a mammal, comprising:
   a) administering Substance-P intravenously to a mammal followed by,
   b) isolating mesenchymal stem cells (MSCs) from the bone marrow of the mammal of a), and
   c) administering the MSCs to a mammal with a corneal wound intravenously to the ear such that the corneal wound is healed.

2. The method of claim 1, wherein the mammal of a) or c) is a human.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtacctccac catgccaagt                                              20
```

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aatgctttct ccgctctgaa                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaactggcag aagaggcact                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtgggtgagg agcacgtagt                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctgcttcca aacctttgac                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aggccacagg tattttgtcg                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcgatgccaa cgatgatcta                                              20

<210> SEQ ID NO 8

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agttctgcat tgcgcttctt                                              20
```